United States Patent [19]

Güenther et al.

[11] 4,136,450
[45] Jan. 30, 1979

[54] HYDRAULIC-PNEUMATIC CONTROL DEVICE FOR CONTROLLING THE FLOW OF AGENTS TO HAND-HELD DENTAL APPARATUS

[75] Inventors: Werner Güenther, Bensheim; Franz Stüeber, Bensheim-Auerbach; Manfred Müether; Hans-Michael Kratochwilla, both of Bensheim, all of Germany

[73] Assignee: Siemens Aktiengesellschaft, Berlin & Munich, Germany

[21] Appl. No.: 720,251

[22] Filed: Sep. 3, 1976

[30] Foreign Application Priority Data

Sep. 22, 1975 [DE] Fed. Rep. of Germany ....... 2542177

[51] Int. Cl.² ............................................ A61C 19/02
[52] U.S. Cl. ...................... 32/22; 137/883; 137/884; 137/885
[58] Field of Search ...................... 32/22; 137/608, 112

[56] References Cited

U.S. PATENT DOCUMENTS

| 2,354,791 | 8/1944 | Boldt ..................................... 137/112 |
| 3,195,572 | 7/1965 | Carls ..................................... 137/608 |
| 3,638,310 | 2/1972 | Austin ..................................... 32/22 |
| 3,665,682 | 5/1972 | Ciavattoni et al. .................. 137/608 |
| 3,673,709 | 7/1972 | Page ..................................... 32/22 |
| 3,707,989 | 1/1973 | Davin ..................................... 137/608 |
| 3,718,974 | 3/1973 | Buchtel et al. ......................... 32/22 |
| 3,766,943 | 10/1973 | Murata ................................... 137/608 |
| 3,872,593 | 3/1975 | Thornton et al. ...................... 32/22 |
| 3,875,958 | 4/1975 | Miller ...................................... 32/22 |
| 3,918,161 | 11/1975 | Morgan et al. ......................... 32/22 |

FOREIGN PATENT DOCUMENTS 868247 5/1961 United Kingdom ...................... 32/28

Primary Examiner—Russell R. Kinsey
Assistant Examiner—John J. Wilson
Attorney, Agent, or Firm—Hill, Gross, Simpson, Van Santen, Steadman, Chiara & Simpson

[57] ABSTRACT

A hydraulic-pneumatic control device characterized by a narrow elongated supply strip having a plurality of channels extending parallel to a longitudinal axis of the strip, a plurality of separate groups of openings spaced along the strip with each group having an opening in communication with each channel, a connecting block having a plurality of separate passages mounted on the strip with the passages in communication with the channels and a control block for each of the dental apparatuses whose agents are being regulated. Each of the control blocks is mounted on the separate group of openings of the supply strip for receiving agents from the channels therein and each block has pneumatically actuated valves for regulating the flow of the agent therethrough.

7 Claims, 2 Drawing Figures

4,136,450

HYDRAULIC-PNEUMATIC CONTROL DEVICE FOR CONTROLLING THE FLOW OF AGENTS TO HAND-HELD DENTAL APPARATUS

BACKGROUND OF THE INVENTION

1. Field of the Invention

The present invention is directed to a hydraulic-pneumatic control device for controlling the flow of agents in hand-held dental apparatuses such as dental handpieces and dental spray devices.

2. Prior Art

Previously when more than one hand-held dental apparatus such as one or two dental handpieces along with a spray device were mounted together, the control devices for the apparatuses had individual components for controlling the flow of an agent to each apparatus and these individual components were fastened such as by bolts directly to one another. Thus, they formed an elongated block wherein the agents were conveyed through the entire block and all of the components and were tapped and removed at the desired locations respectively. Since the entire block must be disassembled in case of a possible defect of one of the components situated in the block or in case of adding an additional component or in case of replacing the components for a dental apparatus, the joining together of all the components into a single block does not allow easy maintenance of the control components or easy addition or replacement of a control component. An additional disadvantage is that a relatively large amount of space is required in order to mount the components in an apparatus and to allow for dismantling of the components.

SUMMARY OF THE INVENTION

The present invention is to provide a hydraulic-pneumatic control device for controlling agents supplied to dental apparatuses which control device is simply constructed of a plurality of modular units, can be housed with space economy in the apparatus, and will enable simple addition or replacement of a control unit as a dental apparatus is added or replaced.

To accomplish these tasks, the hydraulic-pneumatic control device for regulating the flow of agents to at least one hand-held dental apparatus comprises a narrow elongated supply strip having a plurality of channels extending parallel to a longitudinal axis of the supply strip, said supply strip having a plurality of spaced group of openings spaced along the strip with each group having an opening in communication with each channel, a connecting block having a plurality of separate passages for supplying agents to the supply strip, said connecting block being secured on the supply strip with the separate passages in communication with selected channels of the strip, and a control block for each of the dental apparatuses whose agents are being regulated, each of said control blocks being mounted on a separate group of openings of the supply channel for receiving agents from the channels, each of said control blocks having pneumatically actuated valves for regulating the flow of the agents therethrough.

In determining the number of control units for mounting on the strip, the demand frequently made by customers for individual assemblies of hand-held dental apparatuses is taken into account. Practically speaking, the demand can vary between the use of only one drilling and spray handpiece to the use of six handpieces. An additional object of the invention is to construct a control device so that it can be operated in a purely pneumatic fashion without requiring electrical components.

Further advantages and details of the invention will be evident from the following detailed description of the preferred embodiment and the illustration in the attached drawings.

DESCRIPTION OF THE PREFERRED EMBODIMENTS

Figure 1:
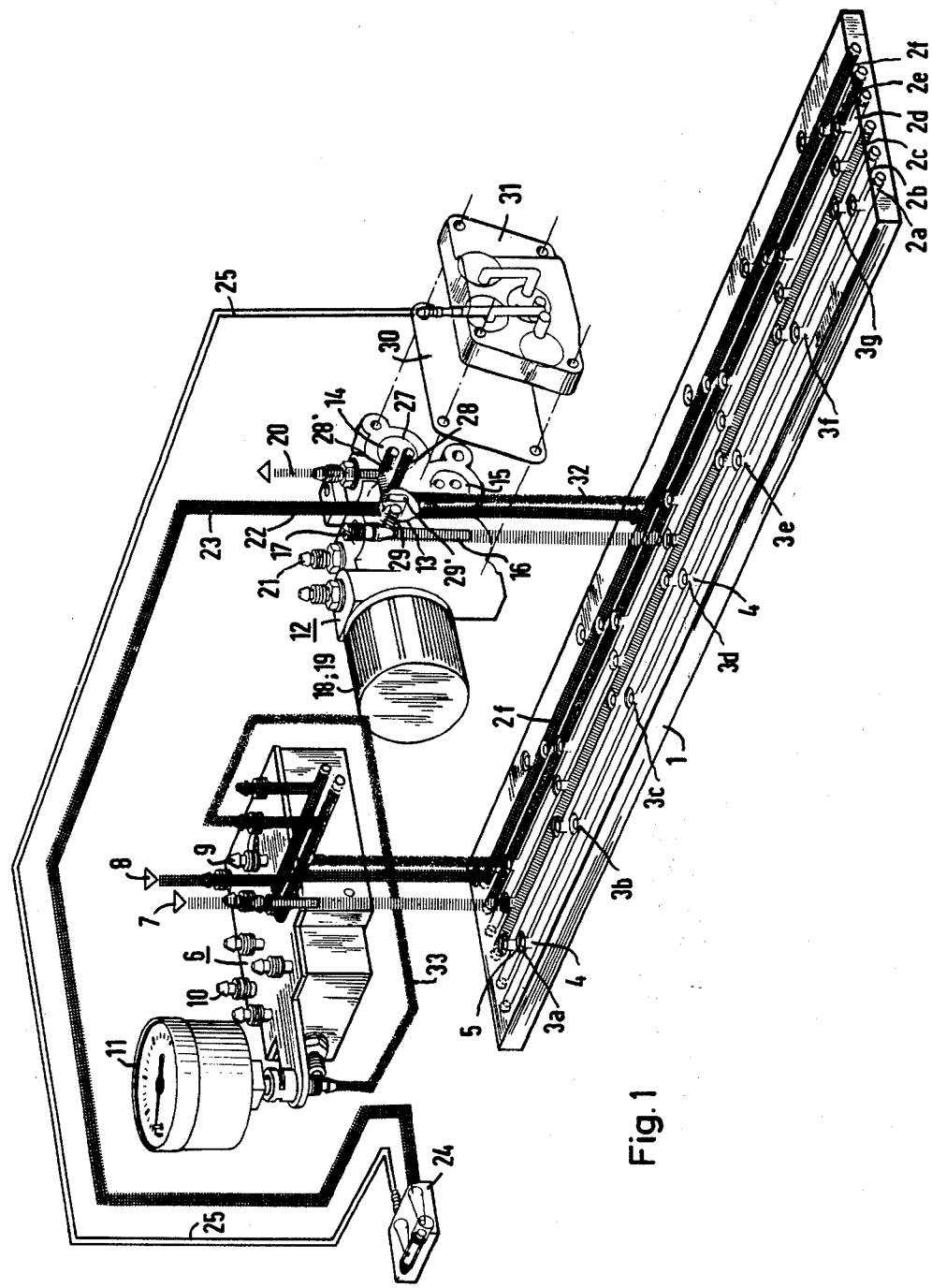
FIG. 1 is an exploded perspective view of a hydraulic-pneumatic regulating device in accordance with the present invention with the flow path of several agents diagrammically illustrated.
Figure 2:
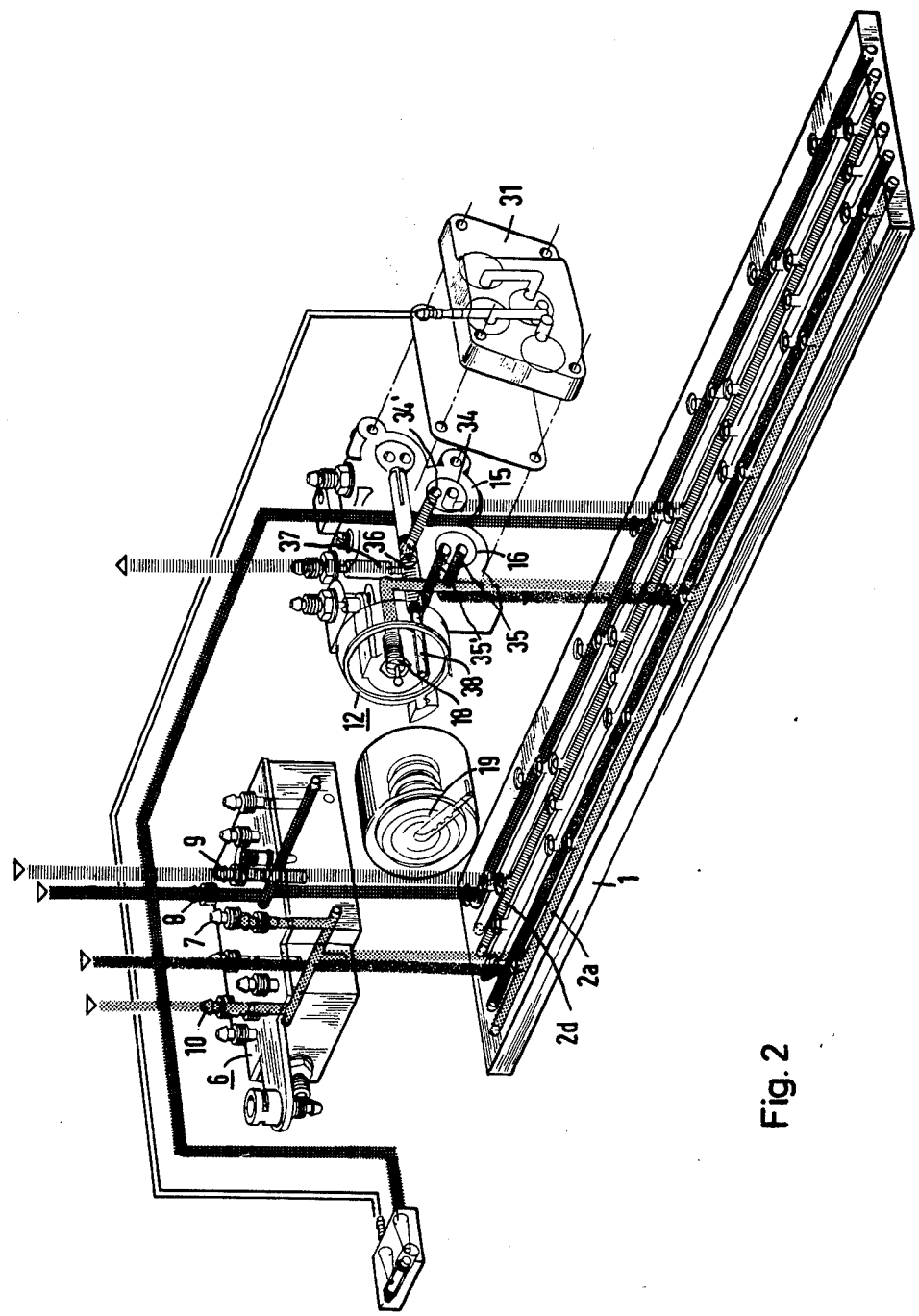
FIG. 2 is an exploded perspective view of FIG. 1 illustrating a flow of different agents in the device.

The principles of the present invention particularly useful in a hydraulic-pneumatic control device generally indicated at 100 in FIGS. 1 and 2. The control device 100 is provided to regulate the flow of agents to one or more dental apparatuses which can include handpieces with a turbine drive and mouth spray devices.

The device 100 contains a narrow elongated supply strip 1 which is approximately 8 mm thick and 50 mm wide. The strip 1 contains a plurality of channels which extend parallel to the longitudinal axis of the strip and as illustrated are six channels 2a–2f. Preferably, the strip is an extruded strip of synthetic material which has the end of the channels 2a–2f sealed by means of a heat sealing process. On the top of the supply strip 1, a plurality of groups of openings 3a–3g are provided with an equal spacing from one another for example approximately 55 mm. Each of the groups contains six transverse bores 4 which are connected with the channels 2a–2f. Each of the bores 4 is provided with a depression 5 such as a counterbore or countersink which receives a sealing gasket or ring (not illustrated). Thus, each group such as 3a will have a bore 4 in communication with each of the channels 2a–2f.

The device 100 includes a connecting block 6 which is formed of synthetic material and which on a top surface is provided with fittings 7–10, 40 and 41 as well as a manometer 11. Each of the fittings 7–10, 40 and 41 is in communication with transit channels or passageways which are not illustrated in great detail, and which channels lead to connecting ports or pieces on a lower surface of the connecting block 6. The connecting pieces on the lower surface are arranged in exact interval of the openings 4 of the group of openings 3a so that when the connecting block is mounted or secured on the supply strip, the transit channels are connected with the corresponding bores 4 in the supply strip. Instead of mounting the block directly at one of the group of openings 3a–3g, it is possible to interconnect the channels of the block 6 to one of the ends of the channels 2a–2f of the strip 1 by appropriate conduits.

The connecting block 6 has the task of either directly conveying to a manual dental tool the agents arriving from non-illustrated supply sources or from a foot control device, respectively, or if it is a question of agents which are to be regulated, feeding these agents directly into channels of the supply strips 1 so that the agents can be distributed to individual components. In addition, the operating pressure for water and/or air, which pressure is required in order to operate the respective apparatus, is indicated on the manometers 11 of the connecting block 6 at all times.

As illustrated in FIG. 1, drive air is applied to the connecting block 6 via the connecting fitting 7 and is conveyed through the block and applied into channel 2c of the strip 1. A regulating or control air is applied to the block by the fitting 8 and is conveyed through the block to be applied in channel 2f of the strip. A socalled "chip blower air", which is a term utilized to designate dry air which is required mainly for drying and for blowing out a cavity, is applied or fed to the control block 6 by the fitting 9 and is communicated through the block 6 to channel 2d of the strip 1. A corresponding switch-on and switch -off valve for the "chip blower" air is usually located on a foot control device. In addition to the above fluids, spray water is supplied to the fitting 10 and through the block 6 to channel 2a of the strip 1 and spray air is supplied by the fitting 40 and is communicated to channel 2b of the strip 1.

For each of the dental apparatuses, a control block 12 is provided. As illustrated, the control block 12 has four valves 13–16, a choke valve 17 and an additional valve 18 which is housed with a return suction flow device 19. The control block 12 on a lower surface is provided with a connected piece which will fit into the transverse bores 4 of a group of openings such as group 3d when the block is secured onto the supply strip 1. As illustrated, the control block 12 has three fittings 20, 21 and 22 on an upper surface. Fitting 20 is connected to a drive air line which will lead to the dental apparatus, fitting 21 is connected to a chip blower line leading to the dental apparatus, and fitting 22 is connected to a control line 23 which leads to a three-way valve 24 which has a return line 25 leading to a fitting 26 on a cover plate 31.

The valve 24 is positioned or assembled in a known fashion in a storage or repository device for the respective dental apparatus so that the valve is actuated by the removing and replacing of the apparatus in the storage device. When the dental apparatus is placed in the storage device, the valve is actuated by a cam lever to charge the conduit 25 with control air from the conduit 23. Upon removal of the apparatus from the device, the valve will be shifted to a position to simultaneously empty or bleed the control air from the line 25. This switching condition is illustrated in the figures.

The housing or casing of the control block 12 contains a lateral surface 27 on which each of the valves 13–16 are disposed. As illustrated, channels 28 and 28' of valve 14 and channels 29 and 29' of valve 13 open onto the lateral surface 27. The openings of these channels may be either aligned side-by-side or one above the other. A membrane 30 covers the surface 27 and is held thereon by the cover plate 31 which has a depression or cavity aligned with each valve 13–16. When a charge of control air in the conduit 25 is applied to the fitting 26, it flows into the cavities on one side of the membrane and forces the membrane against all four valves surfaces the seal all channels of the four valves such as the channels 28, 28' and 29 and 29'.

If the hand tool is placed in the storage device, valve 24 is open to interconnect line 23 with line 25 to convey the control air to be applied against the membrane 30. All four valves 13–16 are then closed. If the hand tool is removed, valve 24 is actuated to vent the line 25. The pressure of the respective working agents such as the drive air and the manometer air which are applied to the channel such as 28, 28' or 29 and 29' will force the membrane toward the cover plate 31 so that the path from channel 28 to 28' or 29 to 29' is opened. The other valves such as 15 and 16 function in an analogous manner.

Drive air which is in the channel 2c of the strip 1 is applied to channel 29 after it passes a choke 17. Channel 29' is connected with a fitting 20 which will receive a conduit or tube leading to the dental apparatus and channel 29' is also in communication with channel 28'. When the valve 14 is open, air in the channel 28' will be conveyed to the channel 28 and then to a line 32 which extends to channel 2e of the supply strip 1. From the channel 2e, this air will pass through the connecting block 6 out of fitting 41 into conduit or line 33 which extends to a fitting on the manometer 11. Thus, the pressure of the drive air will be indicated on the manometer. Adjustments in operating pressure of the drive air is accomplished by means of the choke 17 and due to the indication of the pressure on the manometer 11, the deired air pressure for the drive air can be obtained In FIG. 2, the flow path of the chip blower air, spray water and spray air are illustrated. The spray water as mentioned hereinabove, is connected by fitting 10 and conveyed to the control block 12 by the channel 2a of the strip 1. As the water enters the control block 12, it is applied against the valve 18, which is open via a conductance path, which is not more closely designated, upon being charged with control air. Upon closing of the valve 18, the water located in the line section leading to the dental appatatus is sucked back to a great extent via a return suction flow device 19 which may be a spring loaded membrane.

The chip blower air is conveyed to the supply strip 1 by the connecting fitting 9 and is conveyed to control block 12 via channel 2d. The chip blower air enters the valve 15 by a passage or feed channel 34 and leaves by an adjacent discharge channel or outlet passage 34'. In a similar manner, spray air in channel 2b of the strip 1 is applied to channel 35 of the valve 16 of the control block 12 and it is removed by a drain channel or discharge outlet passage 35'. The outlet passages 34' and 35' are interconnected by a common channel 36 which has a branch or a supply channel 37 that extends to the fitting 21. Thus, either chip blower air or spray air can be conveyed to the dental apparatus. In channel 36, a control piston 38 is disposed with one side being charged with the spray air and the other side being charged with the chip blower air. The control piston 38 has an OR-function. When it is charged with spray air from the passage 35', the control piston 38 is moved from its illustrated position toward the right until it reaches a limit stop at which point it will close or seal the path from the channel 34' to channel 37, but however leaves an open connection between channel 35' and channel 37. When it is charged with chip blower air, it is again brought to the illustrated position where it leaves the path of the channel 34' open to the channel 37 and seals or blocks the path from channel 35 ' to the channel 37. Thus, either spray air or chip blower air can be conveyed to the hand tool by a common line connected to the fitting 21.

Each control block 1 is an individual unit that contains the valves for regulating the drive air, spray air, chip blower air, and manometer air as well as the valve for supplying spray water and in addition a return suction device. The control block has a common control or regulation of all the valves by the membrane such as 30. Since all the components are contained in a single control block, which is mounted on the strip 1, replacement of the control device is possibly at any time. The free groups of openings 3b, 3c and 3e–3g (see FIG. 1) are provided to enable the attachment of additional control blocks for the purpose of controlling the flow of agents to additional dental apparatuses. Thus, the strip 1 can receive up to a maximum of six control blocks for six dental apparatuses. For the groups of openings, which are not being utilized such as the group 3b, O-rings or gaskets are inserted in the depressions 5 for each of the bores 4 and a cover plate is secured to close off the unused openings.

As pointed out hereinabove, the device 100 enables a single control device having a modular control block which block can be added and substracted or replaced as desired. Thus, an installation having one or more control blocks for controlling one or more dental apparatuses can have an additional apparatus added by merely attaching an additional control block at one of the previously unused groups of openings.

Although minor modifications may be suggested by those versed in the art, it should be understood that we wish to employ within the scope of the patent warranted hereon, all such modifications as reasonably and properly come within the scope of our contribution to the art.

We claim:

1. A hydraulic-pneumatic control device for regulating the flow of agents to at least one hand-held dental apparatus, said device comprising a narrow, one piece, elongated supply strip having a plurality of channels extending from one end to the other end and parallel to a longitudinal axis of the supply strip, said supply strip having a plurality of separate groups of openings spaced along the strip with each group having an opening in communication with each channel; a connecting block having a plurality of separate passages for supplying agents to the supply strip, said block being secured on the supply strip with the separate passages in communication with selected channels of the strip; a control block for each of said dental apparatuses whose agents are being regulated, each of said control blocks having channels and being mounted on a separate group of openings of the supply strip with the channels of the control block receiving agents from the channels of the supply strip, each of said control blocks having pneumatically actuated valves for regulating the flow of the agent therethrough, each of said control blocks having a first channels receiving spray air and extending to a first valve of said valves, a second channel receiving chip blower air extending to a second valve of said valves, said first valve having a first outlet passage, said second valve having a second outlet passage, a line channel interconnecting said first and second outlet passages, a supply channel extending from said line channel for communication with a dental apparatus, and a control piston being disposed in the line channel with chip blower air acting on one side and spray air acting on the other side, said piston being movable in the line channel between a first position blocking flow from the second outlet passage and permitting flow from the first outlet passage to the supply channel and a second position blocking flow from the first discharge passage and permitting flow from the second discharge passage to the supply channel so that an application of a charge of chip blower air forces said piston to the second position to permit flow of the chip blower air to the supply channel and an application of a charge of spray air moves the piston to the first position permitting flow of the spray air to the supply channel; and means for sealing the ends of the channels of the supply strip and any of said groups of openings which are free of one of said blocks.

2. A device according to claim 1 wherein the supply strip is an extruded member consisting of synthetic material.

3. A device according to claim 1, wherein a water valve with a return suction device is provided on the control block.

4. A hydraulic-pneumatic control device for regulating the flow of agents to at least one hand-held dental apparatus, said device comprising a narrow, one piece, elongated supply strip having a plurality of channels extending from one end to the other end and parallel to a longitudinal axis of the supply strip, said supply strip having a plurality of separate groups of openings spaced along the strip with each group having an opening in communication with each channel; a connecting block having a manometer and a plurality of separate passages for supplying agents to the supply strip, said blocks being secured on the supply strip with the separate passages in communication with selected channels of the strip; a control block for each of said dental apparatuses whose agents are being regulated, each of said control blocks having channels and being mounted on a separate group of openings of the supply strip with the channels of the control block receiving agents from the channels of the supply strip, each of said control blocks having pneumatically actuated valves for regulating the flow of the agent therethrough, each of said control blocks having a passageway in communication with a channel of the strip charged with compressed air as an agent for a dental apparatus, a channel extending from said passageway in the control block through a choke valve to another channel in the strip in communication with the manometer so that the manometer on the connecting block can be utilized to register an indication of the pressure of the compressed air being conveyed to the dental apparatus from each control block and means for sealing the ends of the channels of the supply strip and any of said groups of openings which are free of one of said blocks.

5. A hydraulic-pneumatic control device for regulating the flow of agents to at least one hand-held dental apparatus, said device comprising a narrow, one piece, elongated supply strip having a plurality of channels extending from one end to the other end and parallel to a longitudinal axis of the supply strip, said supply strip having a plurality of separate groups of openings spaced along the strip with each group having an opening in communication with each channel; a connecting block having a plurality of separate passages for supplying agents to the supply strip; said block being secured on the supply strip with the separate passages in communication with selected channels of the strip; a control block for each of said dental apparatuses whose agents are being regulated, each of said control blocks having channels and being mounted on a separate group of openings of the supply strip with the channels of the control block receiving agents from the channels of the supply strip, each of said control blocks having pneumatically actuated diaphragm valves for regulating the flow of the agent therethrough, each of the diaphragm valves being disposed on a common external surface of the control block and having a feed line channel and an outlet passage arranged with openings arranged adjacent each other on said external surface, a common membrane being disposed on said external surface, a cover plate mounted on the external surface to hold the membrane between the surface and the cover, said cover having a fitting receiving control air to apply pressure on said common membrane to simultaneously close all of said diaphragm valves, each of said control blocks having a channel receiving spray air extending to one of said diaphragm valves, another channel receiving chip blower air extending to a second one of said diaphrahm valves, a line channel interconnecting the outlet passages of the diaphragm valves associated with the spray air and the chip blower air, a supply channel extending from the line channel for communication with a dental apparatus, a control piston disposed in the line channel with the chip blower air acting on one side and the spray air acting on another side, said piston being movable from a first position blocking flow on the chip blower air and permitting flow of the spray air to the supply channel and a second position blocking flow of the spray air and permitting flow of the chip blower air to the supply channel, and means for sealing the ends of the channels of the supply strip and any of said groups of openings which are 6. A device according to claim 5, wherein the supply strip is an extruded member consisting of synthetic material.

7. A device according to claim 5, wherein the control block includes a water control valve with a return suction device.

* * * * *